United States Patent
Cope et al.

(10) Patent No.: US 7,544,184 B2
(45) Date of Patent: Jun. 9, 2009

(54) BLOODLESS PERCUTANEOUS INSERTION SYSTEM

(75) Inventors: Constantin Cope, Bend, OR (US); Mark A. Magnuson, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 766 days.

(21) Appl. No.: 10/813,806

(22) Filed: Mar. 31, 2004

(65) Prior Publication Data

US 2005/0033238 A1 Feb. 10, 2005

Related U.S. Application Data

(60) Provisional application No. 60/460,440, filed on Apr. 4, 2003.

(51) Int. Cl.
*A61M 5/00* (2006.01)
(52) U.S. Cl. .............. 604/167.01; 604/164.01; 604/164.13; 604/167.06
(58) Field of Classification Search ........... 604/167.01, 604/164.01, 164.06, 164.07, 168.01, 523, 604/167.06
See application file for complete search history.

(56) References Cited

U.S. PATENT DOCUMENTS

| | | | |
|---|---|---|---|
| 5,045,065 A * | 9/1991 | Raulerson | 604/158 |
| 5,122,121 A | 6/1992 | Sos et al. | |
| 5,295,970 A * | 3/1994 | Clinton et al. | 604/168.01 |
| 5,395,347 A | 3/1995 | Blecher et al. | |
| 5,407,434 A * | 4/1995 | Gross | 604/167.02 |
| 5,438,993 A * | 8/1995 | Lynch et al. | 600/434 |
| 5,772,607 A | 6/1998 | Magram | |
| 5,984,895 A * | 11/1999 | Padilla et al. | 604/168.01 |
| 6,551,281 B1 * | 4/2003 | Raulerson et al. | 604/164.13 |
| 6,699,221 B2 * | 3/2004 | Vaillancourt | 604/167.01 |
| 2003/0216771 A1 * | 11/2003 | Osypka et al. | 606/191 |

OTHER PUBLICATIONS

"Pulse-Vu Needle, New Design for Arterial Entry," *AngioDynamics*, Division of E-Z-EM, Inc., Queensbury, NY, 1994.
"Sos Bloodless Entry Needle, Unique Closed System Minimizes Physician Contact with Blood," *AngioDynamics*, Division of E-Z-EM, Inc., Glens Falls, NY, 1991.

* cited by examiner

*Primary Examiner*—Nicholas D Lucchesi
*Assistant Examiner*—Laura A Bouchelle
(74) *Attorney, Agent, or Firm*—Brinks Hofer Gilson & Lione

(57) ABSTRACT

A system for permitting substantially bloodless percutaneous entry into an artery or vein of a patient. The system comprises a needle assembly, a needle hub attachment assembly having a hemostatic segment, and a wire guide inserter (curve straightener) or a wire guide holder also having a hemostatic segment. The components are assembled in a leak-free arrangement, and a fluid passageway for withdrawing blood is established through the system. Each of the hemostatic segments opens to permit passage of a wire guide therethrough, but re-seals to prevent flow of blood therethrough. The needle hub attachment assembly preferably includes a fluid-receiving chamber to permit the clinician to see the first squirt of blood as it enters the system.

16 Claims, 5 Drawing Sheets

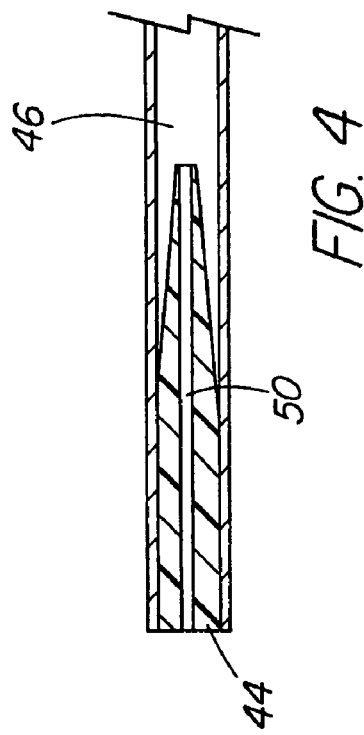
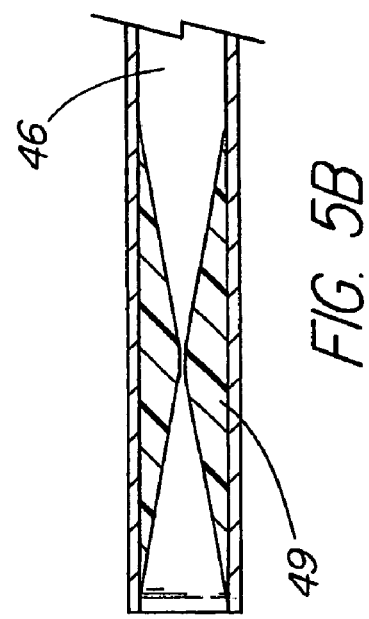
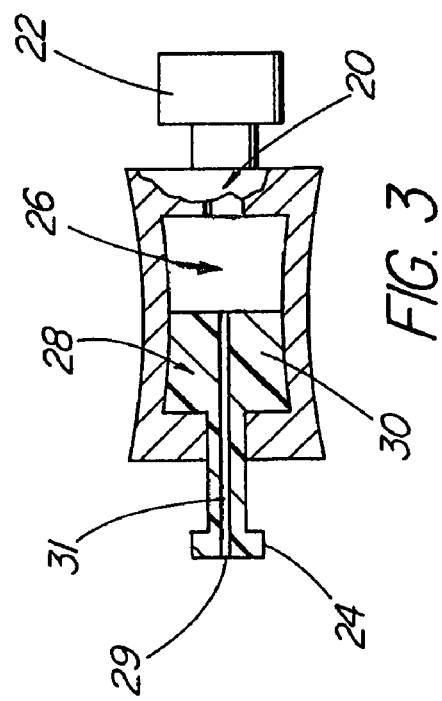
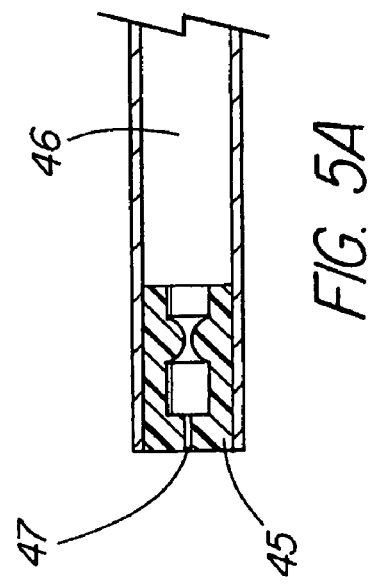
FIG. 3
FIG. 4
FIG. 5A
FIG. 5B

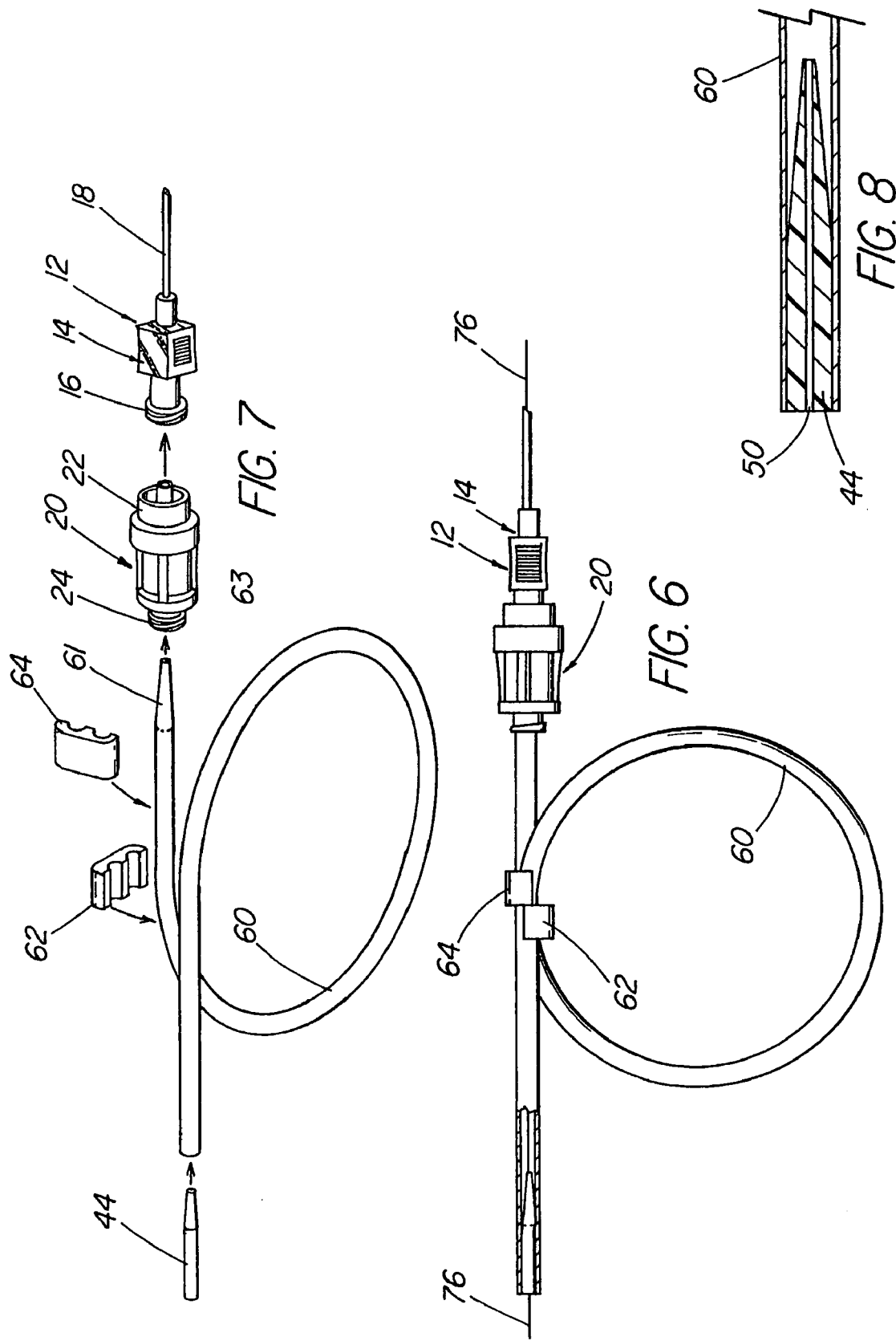

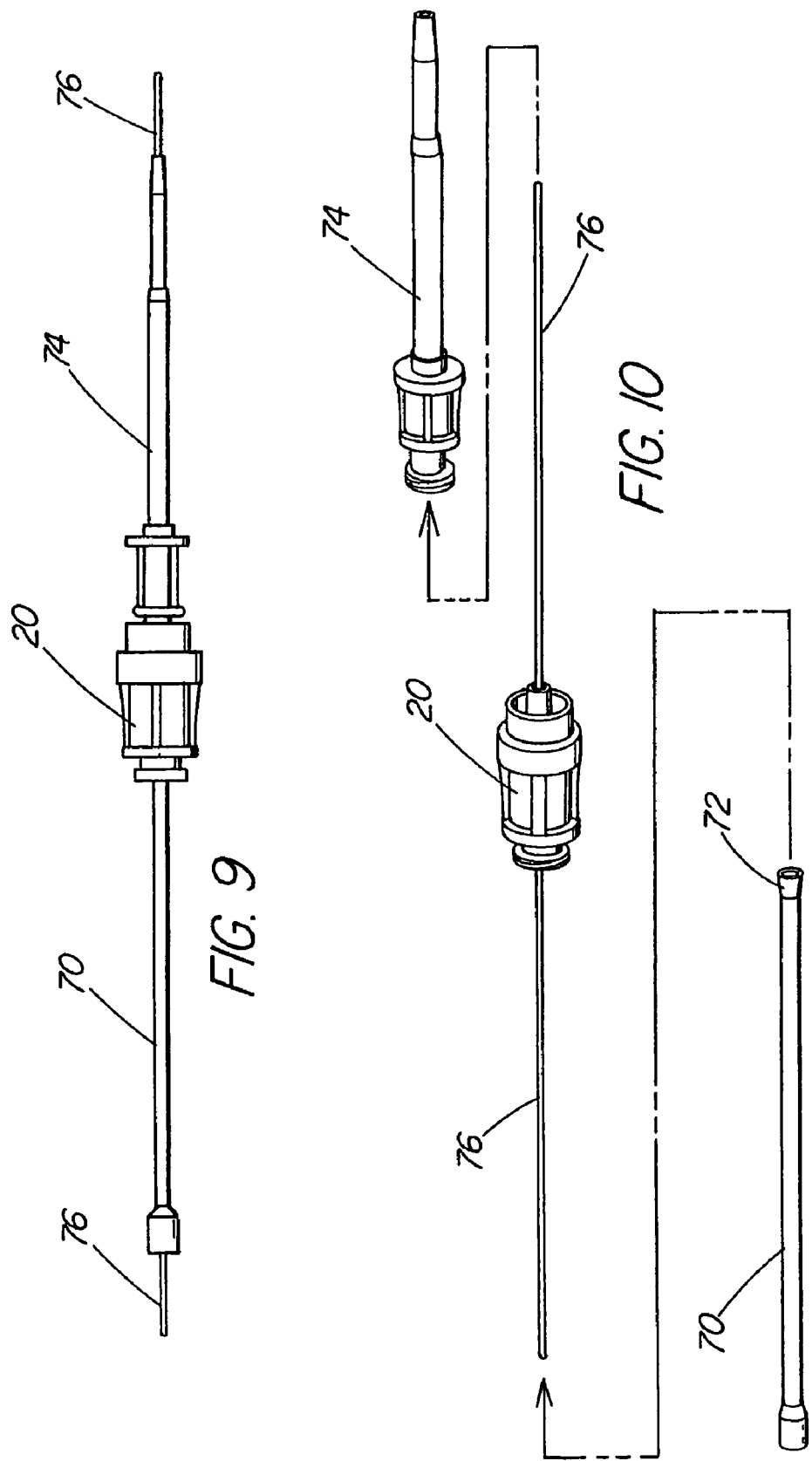

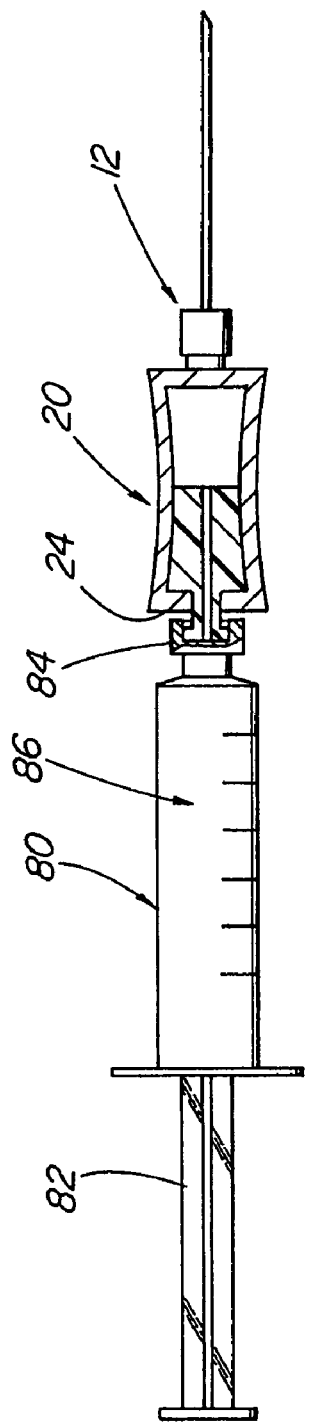
FIG. 11
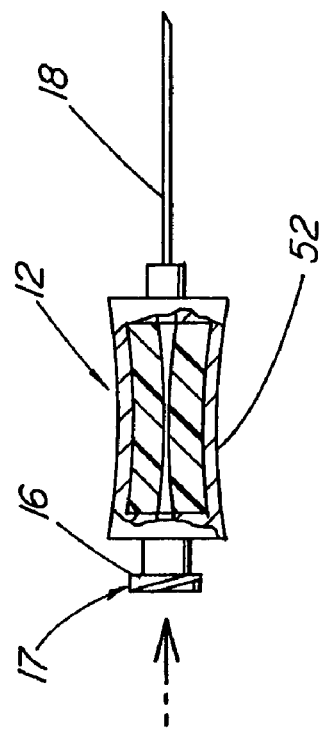
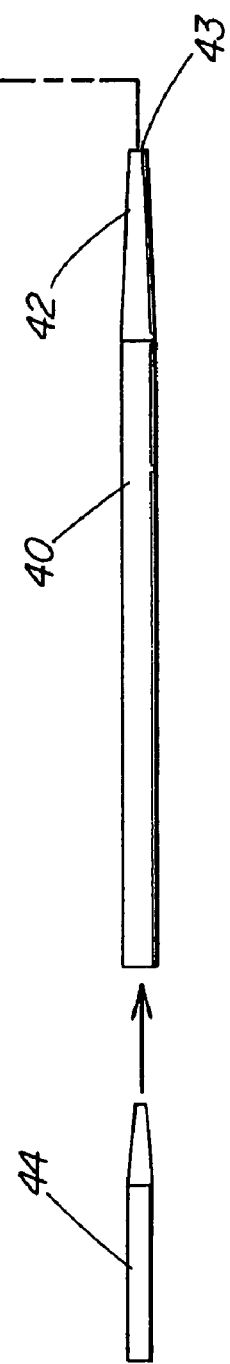
FIG. 12

BLOODLESS PERCUTANEOUS INSERTION SYSTEM

RELATED APPLICATIONS

The present patent document claims the benefit of the filing date under 35 U.S.C. §119(e) of Provisional U.S. Patent Application Ser. No. 60/460,440, filed Apr. 4, 2003, which is hereby incorporated by reference.

BACKGROUND

The present invention relates to a percutaneous entry system, and more particularly, to an insertion system for bloodless percutaneous entry into a body vessel.

In the 1960's and 1970's percutaneous entry procedures for accessing body vessels were gaining increased importance in the medical field. During that time period, exposure of the clinician to blood during such percutaneous entry procedures was normally not a major concern. In the typical percutaneous entry procedure, the clinician would insert a needle through the skin and into a body vessel, such as an artery. When a "squirt" of blood shot out of the needle hub, the clinician received visual proof that the needle tip was in the correct location. A wire guide would then be inserted into the needle and passed into the artery. If a curved, or J-tipped, wire guide was used, a straightener or J-wire inserter was first placed in the needle hub. The wire guide was then passed through the inserter into the needle. With this arrangement the wire guide occluded the needle fairly well. However some blood was still able to seep out through the needle around the wire guide. Following insertion of the wire guide, the needle was removed, and the catheter or introducer sheath was advanced over the wire and into the artery.

At the time that these procedures were in common usage, seepage of a small amount of blood was considered acceptable. However, in later years, blood borne pathogens, such as hepatitis and HIV, became a major concern in the health care environment. Applicable regulations now mandate that health care providers utilize medical devices that eliminate or reduce the risk of exposure to blood whenever a suitable safety device is available.

Several commercial devices have been introduced to limit the exposure to blood during a medical procedure. Currently available products to control the escape of blood into the field of entry are generally aimed at controlling the first "squirt" of blood that passes through the needle when the needle is inserted into the artery. Two such devices are marketed commercially by AngioDynamics, Inc., of Queensbury, N.Y., namely the Sos Bloodless Entry Needle and the Pulse-Vu Needle. These devices have hemostatic valves on the needle hub to prevent the escape of the squirt of blood from the needle. A side arm extension tube attaches to a small chamber to collect the blood squirt, thereby providing visual confirmation that the tip of the needle is in the artery. However, when the clinician desires to insert additional apparatus through the hemostatic valve, such as a wire guide curve straightener or inserter, blood is free to pass through the apparatus and out into the field of entry. Blood may continue to leak out through the apparatus until such time as the wire is well into the artery and the apparatus is removed.

It would be desirable to provide a percutaneous insertion system that is substantially bloodless during not only the initial entry of the needle into the artery or vein, but also during the subsequent insertion of other apparatus, such as a wire guide straightener or a dilator.

BRIEF SUMMARY

The present invention addresses the problems of the prior art. In one embodiment thereof, the present invention comprises a percutaneous insertion system comprising a needle assembly, a needle hub attachment assembly, and an assembly that includes a hemostatic segment. The needle assembly has a proximal end, a distal end, and a passageway extending therebetween. The distal end comprises an elongated needle for percutaneous entry into a body vessel for withdrawal of a body fluid, such as blood. The proximal end comprises a needle hub. The needle hub attachment assembly has a proximal end, a distal end, and a passageway extending therebetween. The distal end of the needle hub attachment assembly is sized and configured for leak-free engagement with the needle hub. The needle hub attachment assembly comprises a chamber communicating with the needle assembly for receiving the body fluid. Preferably, the chamber is made of a transparent or translucent composition to enable visual verification of the presence of the fluid in the chamber. The assembly comprising a hemostatic segment has a proximal end, a distal end, and a passageway extending therebetween. This assembly preferably comprises a wire guide inserter or a wire guide holder. The hemostatic segment is positioned in the passageway and has an opening permitting passage of a wire guide. The distal end is sized and configured for leak-free engagement with the proximal end of the needle hub attachment assembly. The passageway is aligned with the needle assembly passageway and the needle hub attachment assembly passageway to form a path for insertion of the wire guide into said body vessel.

In another embodiment, the present invention comprises a percutaneous insertion system comprising a needle assembly, and an assembly comprising a hemostatic segment. The needle assembly has a proximal end, a distal end, and a passageway extending therebetween. The distal end comprises an elongated needle for percutaneous entry into a body vessel for withdrawing a body fluid. The proximal end comprises a hub, and the needle assembly also includes a hemostatic device. The assembly comprising a hemostatic segment has a proximal end, a distal end, and a passageway extending therebetween. The distal end is sized and configured for leak-free engagement with the proximal end of the needle assembly. The passageway is aligned with the needle assembly passageway to form a path for insertion of a wire guide into the body vessel. The hemostatic segment is positioned in the passageway and has an opening permitting passage of a wire guide.

In still another embodiment, the present invention comprises a fluid withdrawal system. The fluid withdrawal system comprises a needle assembly, a needle hub attachment assembly, and a mechanism, such as a syringe, for withdrawing fluid from a body vessel. The needle assembly has a proximal end, a distal end, and a passageway extending therebetween. The distal end comprises an elongated needle for percutaneous entry into a body vessel for withdrawing a body fluid, and the proximal end comprises a needle hub. The needle hub attachment assembly has a proximal end, a distal end, and a passageway extending therebetween. The distal end of the needle hub attachment assembly is sized and configured for leak-free engagement with the needle hub. The needle hub attachment assembly comprises a chamber in communication with the needle assembly for receiving the withdrawn body fluid. The withdrawal device has a proximal end, a distal end and a fluid receptacle therebetween. The proximal end can include a plunger for aspirating the body fluid through the passageways into the receptacle. The distal end is sized and configured for leak-free engagement with the proximal end of the needle hub attachment assembly.

BRIEF DESCRIPTION OF THE DRAWINGS

FIG. 3 is a cross-sectional view of the needle hub attachment assembly shown in FIG. 1.

FIG. 4 is an enlarged view of the proximal end of the wire guide inserter of FIG. 1, showing the presence of a valved hub.

FIGS. 5a and 5b illustrate other embodiments of a hemostatic valve.

FIG. 6 illustrates another embodiment of the inventive system for bloodless percutaneous insertion.

FIG. 7 is an exploded view of the insertion system of FIG. 6.

FIG. 8 is an enlarged view of the proximal end of the wire guide holder of FIG. 6, showing the presence of a valved hub.

FIG. 9 illustrates an alternate embodiment of the inventive system utilizing a reverse flare wire guide inserter.

FIG. 10 is an exploded view of the embodiment of FIG. 9.

FIG. 11 illustrates an alternative embodiment of the inventive system that includes a syringe for aspirating a body fluid from a body vessel.

FIG. 12 illustrates another alternative embodiment of the inventive system.

DETAILED DESCRIPTION OF THE DRAWINGS AND THE PRESENTLY PREFERRED EMBODIMENTS

The presently preferred embodiments of the present invention will be described in detail below with reference to the accompanying drawings. In the description below, the terms "distal" and "proximal" are used in their conventional manner when describing medical devices. The "distal" end of a component refers to the end of the described component that is in closest proximity to the patient when in use. The "proximal" end of a component refers to the end of the component that is at the greatest distance from the patient.

Figure 1:
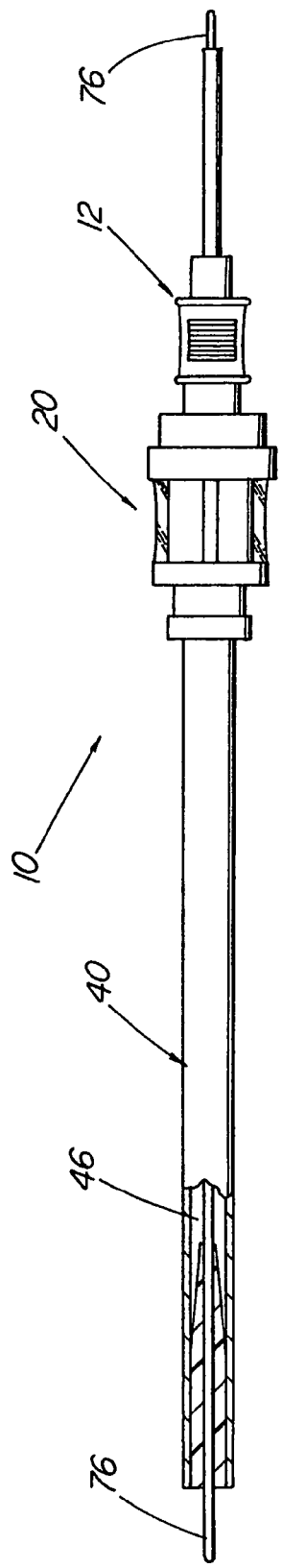
FIG. 1 illustrates a side view of one embodiment of the inventive system for bloodless percutaneous insertion.
Figure 2:
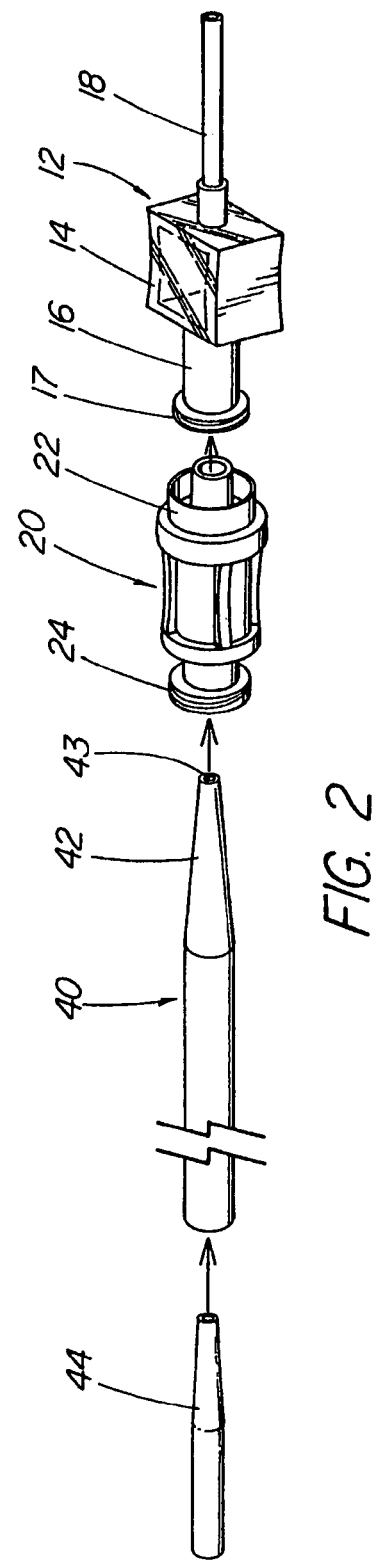
FIG. 2 is an exploded view of the insertion system of FIG. 1.

FIG. 1 illustrates a side view of one embodiment of a percutaneous insertion system 10 according to the present invention. FIG. 2 illustrates an exploded view of the percutaneous insertion system of FIG. 1. In the embodiment shown in these figures, percutaneous insertion system 10 comprises a needle assembly 12, a needle hub attachment assembly 20 and a wire guide inserter (curve straightener) 40. Wire guide inserters are well known in the art for straightening curved interventional devices, such as wire guides, prior to initial entry into the vascular system.

Needle assembly 12 includes a needle hub 14 at its proximal end and an elongated needle 18 at its distal end. In the embodiment shown, needle hub 14 includes a connector 16 for connection with needle hub attachment assembly 20. Needle 18 is sized for percutaneous insertion into a body vessel of a patient, such as an artery or a vein, for use in a medical procedure, such as angiography. Needles suitable for use in the present invention are commercially available in a wide range of sizes. Those skilled in percutaneous entry techniques can readily select a suitably-sized needle for a particular application.

Needle assembly 12 includes a central passageway (not shown) extending longitudinally therethrough for transport of a fluid to or from the patient. The central passageway may also be used for passage of a wire guide 76 into the artery or vein penetrated by the needle. Although the present invention is generally described hereinafter with particular reference to the withdrawal of blood from the patient, those skilled in the art will recognize that the inventive apparatus is also suitable for use with fluids other than blood.

Needle hub attachment assembly 20 includes a connector 22 at its distal end, a connector 24 at its proximal end and a chamber 26 intermediate connectors 22, 24 (FIG. 3). In the embodiment shown, distal connector 22 is sized and configured to mate with needle assembly connector 16 to form a leak-free seal therebetween. Connectors 16 and 22 can be joined by any suitable connection mechanism known in the art to establish a secure leak-free seal in a medical device, such as a threaded connection or a luer lock connection. In the embodiment shown, connector 16 includes thread fittings 17 that are configured to mate with corresponding threads (not shown) on the annular internal surface of connector 22.

Proximal connector 24 is sized and configured to form a leak-proof seal with the distal end of wire guide inserter 40, in a manner to be described. When the device is assembled, needle hub attachment assembly chamber 26 communicates with needle assembly 12 to receive blood from needle assembly 12.

As illustrated in FIG. 3, needle hub attachment assembly 20 further includes a valve 28 for preventing leakage of the body fluid. Preferably, valve 28 is a hemostatic valve of a type well known in the art. In the embodiment shown, valve 28 comprises a plug of elastomeric material 30 of a type generally known in the art for use as a valve material, such as silicone. Valve 28 includes a slit 29 at its proximal end which opens to a self-sealing longitudinal passageway 31 extending through valve 28. The elasticity of valve 28 permits passageway 31 to open when tapered distal end 42 of inserter 40 is inserted therein, and to remain closed in the absence of the inserter. Preferably, at least the outer surface of needle hub attachment assembly 20 is comprised of a transparent or translucent polymer, such as a polycarbonate, to permit visual verification of the presence of blood in the chamber. This enables the clinician to receive positive proof that the needle has entered the artery or the vein.

A device that is particularly suitable for use as a hub attachment assembly in the inventive percutaneous entry system is commercially available from Halkey-Roberts Corporation, of St. Petersburg Fla. This device, known as Swabable Valve 24520040xx, is formed from a polycarbonate or copolyester. This lightweight device mates securely with all standard luer connectors and luer syringes to provide a hermetic seal. The device includes a chamber that communicates with the central passageway of the needle to receive the blood from the needle. In addition, the transparency of the outer covering of the device allows the clinician to visually verify the presence of blood in the chamber. The device includes an elastomeric valve that is sized to readily accept the introduction of the inserter into its proximal end, and allows free, unobstructed passage of the wire guide when the inserter is in place.

Wire guide inserter 40 includes a tapered distal end 42, a hemostatic segment 44 at its proximal end, and a central passageway 46 extending longitudinally through the inserter. Suitable wire guide inserters are commercially available. Such inserters are generally about 5 cm in length, and formed from polyethylene or other plastic. Preferably, inserter distal end 42 tapers to an endhole 43. The tapered end of the inserter is sized such that it can be snugly inserted into the proximal end of the needle hub attachment assembly 20. Endhole 43 has a diameter that substantially matches the diameter of the wire guide to inhibit blood reflux through the device. However, the diameter of endhole 43 may be formed to be slightly larger than that of the wire guide to permit smooth insertion and/or extraction of the wire guide from the inventive system 10.

Hemostatic segment 44 is provided at the proximal end of wire guide inserter 40 to prevent the backflow of blood through the proximal end of the inserter. Segment 44 has a central lumen 50 extending longitudinally therethrough. Preferably segment 44 tapers in the distal direction as shown. The presence of the taper allows blood to collect circumferentially on the exterior of the tapered portion of segment 44 within lumen 46. Any pressure within the system circumferentially will cause the taper to collapse within the lumen, thereby sealing around the wire guide, or sealing completely if no wire guide is present. Preferably, the diameter of central lumen 50 is the same, or substantially the same, as that of endhole 43. In the embodiment shown, hemostatic segment 44 comprises an elongated polyurethane tube having a length of about 1.5 cm. The outer diameter of hemostatic segment 44 is substantially the same as the inner diameter of inserter 40, to establish the leak-free seal.

Other known hemostatic devices can be substituted for segment 44 shown in the figures. Examples of alternative hemostatic segments for the wire guide assembly are conventional hemostatic valves 45 and 49, shown in FIGS. 5a and 5b, respectively. Preferably, valves 45, 49 are formed of an elastomer such as silicone. Valve 45 includes a slit 47 at its proximal end for passage of the wire guide. The valves have a longitudinal passageway that is penetrated by the wire guide as the wire is being introduced into the body vessel. The elastomeric material of the valve conforms to the wire guide to establish, and re-establish if necessary, the leak-free seal.

The percutaneous entry system of FIGS. 1 and 2 is particularly suited for use with long wire guides, such as wire guides having a length from about 60 cm to several hundred centimeters. Such long wire guides are generally packaged in a bulky wire guide holder that normally has no additional functionality. Once the wire guide is inserted via the inventive system and is properly seated in the artery or vein, the system can be withdrawn and discarded, leaving the wire guide in place and ready for further use during a medical procedure.

Another embodiment of the inventive percutaneous entry system is illustrated in FIGS. 6-8. This system is intended for use with shorter wire guides, normally on the order of about 30 to 75 cm. In this embodiment a generally looped wire guide holder 60 is used in place of the elongated wire guide inserter 40 shown in FIGS. 1 and 2. In the present context, a "looped" wire guide holder comprises a holder capable of being arranged in a loop as shown in order to facilitate handling during insertion of the wire guide. Such wire guide holders are well known to those of ordinary skill in the art, and are readily available commercially.

When wire guide holder 60 is looped in a circle as shown in FIGS. 6 and 7, a wire guide can be advanced in the same direction as the needle. In order to inhibit blood reflux, the distal end 61 of wire guide holder 60 tapers to an endhole 63 having a diameter that substantially matches the diameter of the wire guide. The proximal end of wire guide holder 60 includes a hemostatic segment, such as segment 44. Suitable hemostatic segments are known in the art, such as the hemostatic segments identified in the previous embodiment and illustrated in FIGS. 4, 5a and 5b.

Wire guide holder 60 may be configured to be held comfortably with one hand, while holding the needle in the other hand. When a looped wire guide holder is used, clips 62, 64 or similar attachment mechanisms or fasteners can be utilized to maintain the wire guide holder in the looped configuration. Although the wire guide holder 60 shown in FIGS. 6 and 7 has a looped configuration, other configurations are also possible, such as a generally spiral shape or a tear drop shape. These configurations assist the user in controlling the wire guide during the insertion process, and provide a convenient way to restrain the wire guide. If desired, the wire guide holder can be disengaged from the system following insertion of the wire guide into the artery or vein. Removing the wire guide holder assembly enables the physician to further advance the wire guide in the vessel, if desired.

In the embodiments shown, respective tapered distal ends 42 and 61 are shown to be integral with inserter 40 and wire guide holder 60, respectively. However, this is not required. Tapered distal ends 42 and 61 may be provided as initially separate components that are thereafter attached or otherwise mounted at the respective distal ends of inserter 40 and wire guide holder 60.

Other variations of the inventive system are also within the scope of the invention. For example, the needle assembly 12 and the needle hub attachment assembly 20 need not be discrete parts. Rather, they can be combined as a single part. This system can be provided with a wire guide inserter, or with a wire guide holder equipped with a hemostatic segment and pre-loaded with a wire guide.

In another variation, the needle hub attachment assembly 20 can be eliminated, and a wire guide inserter 40 can be attached directly to a needle assembly. This embodiment is shown in FIG. 12. A hemostatic segment 52 can be provided as shown, or alternatively, any of the previously-described hemostatic segments can be used. The hemostatic segment receives the distal end 42 of the inserter 40 to create a leak-free seal between the needle assembly and the distal end. When the needle enters the artery, blood flashback or the "squirt" can be visualized in the inserter. The wire is then advanced through the system into the artery in the normal fashion. Alternatively, a wire guide holder 60 or a syringe (FIG. 11) may be substituted for the wire guide inserter.

Another embodiment of the inventive percutaneous entry system is illustrated in FIGS. 9 and 10. In this embodiment, a wire guide inserter (curve straightener) 70 is provided having a reverse flared distal tip 72. The proximal end of the needle hub attachment assembly 20 is shaped to conform to the reverse flared inserter to establish a secure leak-free connection therebetween. The distal end of the needle hub attachment assembly 20 is connectable to a catheter 74. This arrangement allows the inserter/hub attachment/catheter combination to be readily threaded over a wire guide 76.

The embodiment of FIGS. 9 and 10 facilitates initial catheter insertion as well as catheter changeout, while maintaining hemostatic properties. Catheter changeout may be required when it is determined that the initial catheterization was incorrect, and a new catheter must be substituted for the catheter originally percutaneously placed. This can occur, for example, when it is determined that a curved catheter should be utilized instead of a previously-placed straight catheter.

With the embodiment of FIGS. 9 and 10, the initial needle stick is performed with an apparatus such as shown in any of FIGS. 1-8, 11 and 12. A wire guide is inserted via a wire guide holder or a wire guide inserter. The initial apparatus comprising the needle assembly (with or without a needle hub assembly) and wire guide inserter or wire guide inserter is removed, leaving the wire guide in the patient. The system shown in FIGS. 9 and 10 is then threaded over the wire guide. When wire guide inserter 70 is removed, the system remains bloodless. An advantage of this embodiment is that when catheters are threaded over the wire the physician normally opens up a hole that has a larger diameter than the diameter of the wire, thereby increasing blood loss and the potential release of blood and blood borne pathogens into the field of operation. This system would minimize such loss upon removal of inserter 70.

The inventive system can also utilize a "safety" type needle instead of the needle shown in the figures, so that the point of the needle is covered or protected when it is withdrawn from the patient. This has the added advantage of protecting the workers from inadvertent needle stick. Such needles are well known, and are available commercially from Medamicus Corp., of Minneapolis, Minn., among others.

Another variation of the invention is shown in FIG. 11. In this embodiment, a fluid withdrawal mechanism, such as syringe 80, is initially connected to the proximal end of needle hub attachment assembly 20 in place of the wire guide holder or the inserter. In the embodiment shown, syringe 80 includes a proximal end 82, a distal end 84 and a fluid receptacle 86. Proximal end 82 comprises a plunger for aspirating fluid from the body vessel in well known fashion. Distal end 84 is sized and configured to form a leak-free connection with proximal end 24 of the needle hub attachment assembly. Distal end 84 of syringe 80 and proximal end 24 of the needle hub attachment assembly can be connected by any suitable connection mechanism, such as a threaded connection or a luer lock connection. The distal end of needle hub attachment assembly 20 is connected to the proximal end of a suitably-sized needle assembly 12 in the manner described above.

Withdrawal mechanism 80 can be of any configuration suitable to establish the connections described, and will generally be of a conventional capacity for the purposes to which it is to be utilized. Standard 3 ml or 5 ml syringes provided with a luer end that mates with the luer end of hub attachment assembly 20 are particularly preferred. Such syringes are commercially available from Becton Dickenson, of Franklin Lakes, N.J.

If a vein having low flow is accessed, syringe 80 may be used to aspirate blood from the vein into the barrel chamber of the syringe. If an artery having higher flow is accessed, the barrel of the syringe can be first pulled back to, e.g., the 2 ml mark, and arterial blood then pulses into the barrel chamber. The use of a syringe may be particularly beneficial when blood is to be withdrawn from patients whose blood pressure may be insufficient to naturally aspirate blood into the chamber of the needle hub attachment assembly. As a variation of this embodiment, needle hub attachment assembly 20 may be omitted, or it may be combined with needle assembly 12 as described above.

Those skilled in the art will appreciate that various types (e.g. microguidewire) and lengths (e.g., 40 cm, 60 cm, 125 cm, etc.) of wire guides are suitable for use in the invention. Preferably, the wire guide is of sufficient size that the floppy distal tip of the wire extends about 8-10 cm beyond the distal end of the needle when the distal end of the inserter is fully inserted into the needle hub attachment assembly.

Although it is believed that the inventive percutaneous insertion system will have particular utility in angiographic procedures, the invention is not so limited. Rather, the device can be used anywhere in the body where an external dilated hole is required.

Needles, wire guide straighteners, wire guides, and wire guide holders suitable for use in the percutaneous insertion system of the present invention are commercially available from, e.g., Cook Incorporated, of Bloomington, Ind.

While this invention has been particularly shown and described with reference to preferred embodiments thereof, it will be understood by those skilled in the art that various changes in form and details may be made therein without departing from the spirit and scope of the invention. Those skilled in the art may recognize or be able to ascertain using no more than routine experimentation, many equivalents to the specific embodiments of the invention described specifically herein, which equivalents are intended to be encompassed in the scope of the invention.

What is claimed is:

1. A percutaneous insertion system, comprising:
    a needle assembly having a proximal end, a distal end, and a passageway extending therebetween, the distal end comprising an elongated needle for percutaneous entry into a body vessel for withdrawing a body fluid therefrom, and the proximal end comprising a needle hub;
    a needle hub attachment assembly having a proximal end, a distal end, and a passageway extending therebetween, the distal end of said needle hub attachment assembly sized and configured for leak-free engagement with said needle hub, the needle hub attachment assembly comprising a chamber communicating with said needle assembly for receiving said body fluid, the needle hub attachment assembly comprising an elastomeric valve; and
    an assembly comprising a hemostatic segment, said assembly having a proximal end, a distal end, and a passageway extending therebetween, said hemostatic segment comprising a valve positioned in said passageway at said proximal end of said assembly and having an opening permitting passage of a wire guide therethrough, said distal end sized and configured for leak-free engagement with the proximal end of said needle hub attachment assembly, said passageway aligned with said needle assembly passageway and said needle hub attachment assembly passageway to form a path for insertion of said wire guide into said body vessel, wherein the distal end of said assembly comprising a hemostatic segment tapers to an endhole having a diameter substantially the same as the diameter of the wire guide.

2. The percutaneous insertion system of claim 1, wherein the assembly comprising a hemostatic segment comprises a wire guide inserter.

3. The percutaneous insertion system of claim 1, wherein the assembly comprising a hemostatic segment comprises a wire guide holder.

4. The percutaneous insertion system of claim 3, wherein said wire guide holder is pre-loaded with a wire guide.

5. The percutaneous insertion system of claim 1, wherein said valve comprises an elastomeric valve.

6. The percutaneous insertion system of claim 1, wherein said valve tapers to an endhole having a diameter substantially the same as the diameter of the wire guide.

7. The percutaneous insertion system of claim 1, wherein said tapering distal end of said assembly comprising a hemostatic segment is received in said elastomeric valve of said needle hub attachment assembly.

8. The percutaneous insertion system of claim 1, wherein the needle hub effacement assembly comprises a substantially transparent or translucent outer surface.

9. The percutaneous insertion system of claim 3, wherein the wire guide holder comprises a generally looped configuration, said wire guide holder further comprising fasteners to maintain said holder in the looped configuration.

10. The percutaneous insertion system of claim 1, wherein at least one of said leak-free engagements comprises a luer lock assembly.

11. The percutaneous insertion system of claim 1, wherein at least one of said leak-free engagements comprises a threaded connection.

12. The percutaneous insertion system of claim 1, wherein the distal end of said needle hub attachment is connectable to a catheter.

13. A percutaneous insertion system, comprising:
   a needle assembly having a proximal end, a distal end, and a passageway extending therebetween, the distal end comprising an elongated needle for percutaneous entry into a body vessel for withdrawing a body fluid therefrom, the proximal end comprising a hub, said needle assembly including a first hemostatic segment; and
   an assembly comprising a second hemostatic segment, said assembly having a proximal end, a distal end, and a passageway extending therebetween, said distal end sized and configured for leak-free engagement with the proximal end of said needle assembly, said passageway aligned with said needle assembly passageway to form a path for insertion of a wire guide into said body vessel, said second hemostatic segment comprising a valve positioned in said passageway at said proximal end of said assembly and having an opening permitting passage of said wire guide therethrough, wherein said assembly comprising a second hemostatic segment comprises a wire guide inserter, said wire guide inserter having a reverse flared tip, and wherein the proximal end of said needle assembly is shaped to conform to said reverse flare to comprise said leak-free engagement.

14. The percutaneous insertion system of claim 13, wherein said needle assembly includes a chamber for receiving said body fluid, said chamber being formed of a material having a substantially transparent or translucent outer surface.

15. The percutaneous insertion system of claim 13, wherein at least one of said first and second hemostatic segments comprises an elastomeric valve.

16. The percutaneous insertion system of claim 13, wherein said second hemostatic segment comprises a valve, and wherein said valve tapers to an endhole having a diameter substantially the same as the diameter of the wire guide.

* * * * *

UNITED STATES PATENT AND TRADEMARK OFFICE
CERTIFICATE OF CORRECTION

PATENT NO. : 7,544,184 B2  Page 1 of 1
APPLICATION NO. : 10/813806
DATED : June 9, 2009
INVENTOR(S) : Constantin Cope and Mark A. Magnuson It is certified that error appears in the above-identified patent and that said Letters Patent is hereby corrected as shown below:

In column 8, line 62, please delete "effacement" and insert in lieu thereof
-- attachment --.

Signed and Sealed this

Fourth Day of August, 2009

JOHN DOLL
*Acting Director of the United States Patent and Trademark Office*